United States Patent [19]
Pantic et al.

[11] Patent Number: 5,314,882
[45] Date of Patent: May 24, 1994

[54] METHOD FOR PROMOTING GROWTH AND IMPROVED MEAT QUALITY IN MEAT PRODUCING ANIMALS WITH FEMALE STEROIDAL HORMONES

[75] Inventors: Vladimir Pantic, Belgrade; Nestor Sijacki, Novi Sad; Svetislav Kolaric, Sombor, all of Yugoslavia

[73] Assignee: International Foundation for Biochemical Endocrinology, Boca Raton, Fla.

[21] Appl. No.: 879,104

[22] Filed: May 4, 1992

Related U.S. Application Data

[63] Continuation of Ser. No. 582,774, Sep. 14, 1990, abandoned, which is a continuation of Ser. No. 210,168, Jun. 21, 1988, abandoned, which is a continuation-in-part of Ser. No. 696,563, Jan. 30, 1985, abandoned.

[30] Foreign Application Priority Data

Jan. 3, 1984 [YU] Yugoslavia ............................ 166/84

[51] Int. Cl.$^5$ ............................................. A61K 31/56
[52] U.S. Cl. ................................... 514/170; 514/177; 514/182
[58] Field of Search ................. 514/170, 182, 177, 953

[56] References Cited

U.S. PATENT DOCUMENTS 3,331,356 7/1967 Eckstein .................................. 119/3
3,352,684 11/1967 Gard et al. .............................. 99/4
3,636,211 1/1972 Jordan ................................. 424/240

FOREIGN PATENT DOCUMENTS 0015637 9/1980 European Pat. Off. .
1387841 12/1963 France .
2230378 12/1974 France ............................... 514/170

OTHER PUBLICATIONS

Intensive Beef Production; 2nd Ed. (1974) pp. 288-304; Preston et al.
CA vol. 98 (1983) No. 19 Par. 159540w.
CA vol. 94 (1981) No. 17 Par. 132965u.
CA vol. 90 (1979) No. 3 Par. 21,265p.
CA vol. 70 (1969) No. 13 Par. 54,562y.
B. N. Day et al., Effects of Stilbestrol and a Combination of Progesterone and Estradiol on Growing-Finishing Swine, Missouri Agricultural Experiment Station, Columbia, pp. 898-901, 1960.
J. R. Brethour et al., Implanting Weaned Bull Calves with Zeranol and/or Trenbolone, American Society of Animal Science, Pullman, Wash., Jul. 26-29, 1983, three pages.
G. W. Thrasher et al., The Effect of Estrogenic and Androgenic Compounds Upon Growth and Carcass Composition of Swine, Purdue University Agricultural Experiment Station, Lafayette, Ind., pp. 399-409, 1972.

Primary Examiner—Frederick E. Waddell
Assistant Examiner—K. Weddington

[57] ABSTRACT

The growth rate of meat-producing animals as well as the yield and quality of the meat obtained therefrom is improved by administering to the animal prior to its sexual maturation an effective amount of a female gonadal steroidal compound; namely, an estrogen or progestagen compound and preferably a mixture thereof, sufficient to delay development of the gonadal function of the animal, e.g., spermatogenesis. Such administration is terminated sufficiently prior to slaughter of the animal that the administered steroidal compound has been substantially completely removed from the animal's system which before slaughter exhibits levels of the corresponding natural hormones therein substantially within normal limits. In mammals, administration is preferably by injection, but in fish, shellfish and poultry, the active steroidal compound is incorporated at low levels in the usual feed therefor. In mammals, the treatment is preferably applied to uncastrated males but can be extended to females and castrated males if desired; while in fish, shellfish and poultry administration is without regard to sex. The ratio of lean meat to fat is increased significantly by the treatment and in male mammals aggressiveness and odor development with consequential tainting of the meat is suppressed until slaughter.

10 Claims, 3 Drawing Sheets

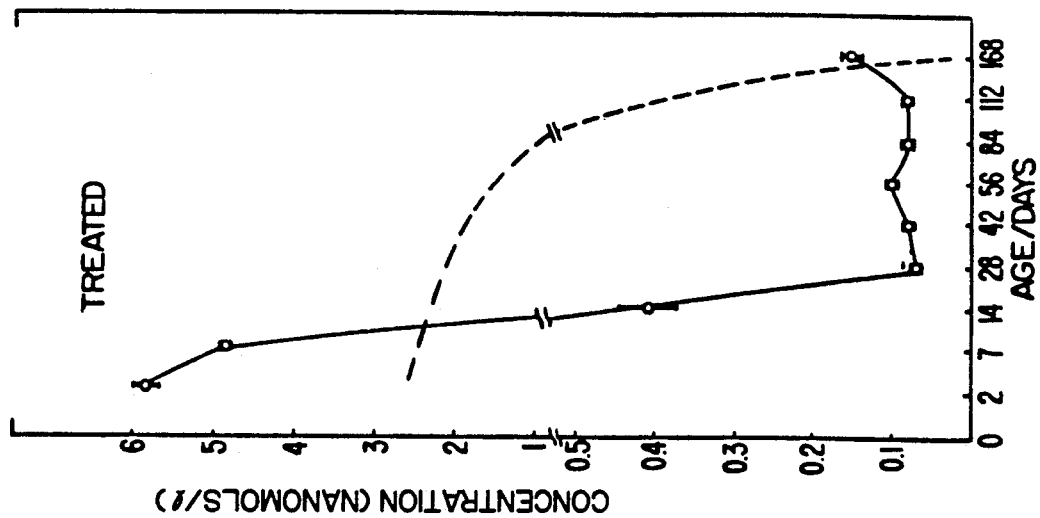
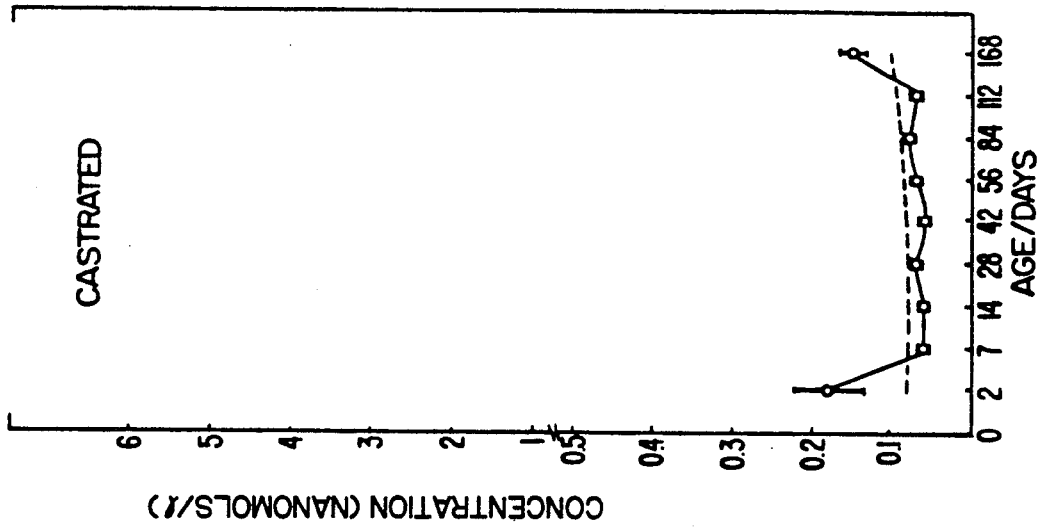
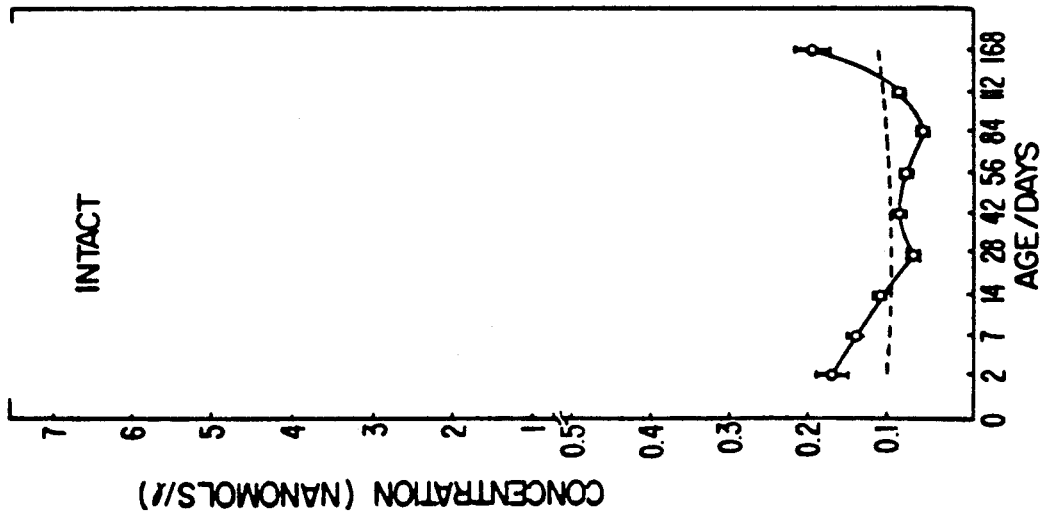

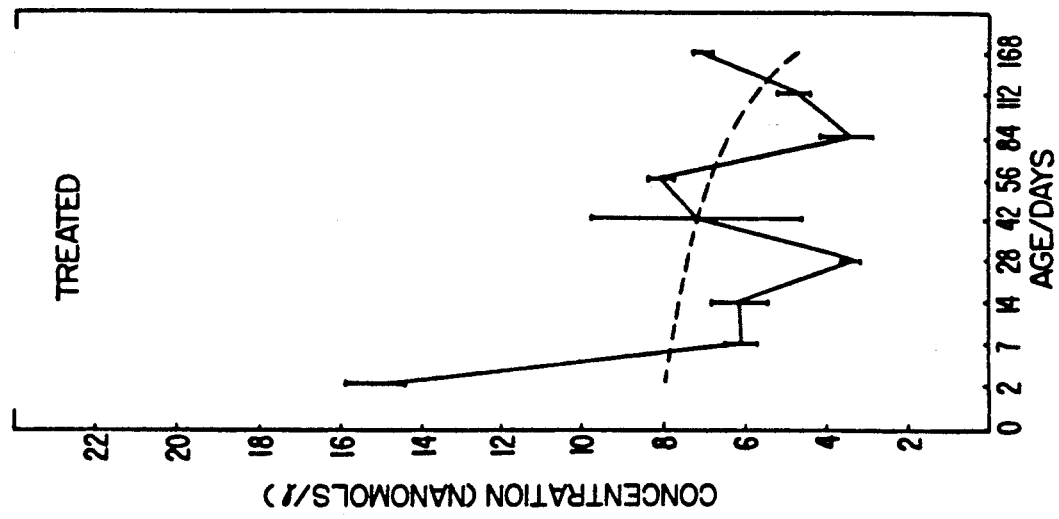
FIG. 2C TREATED
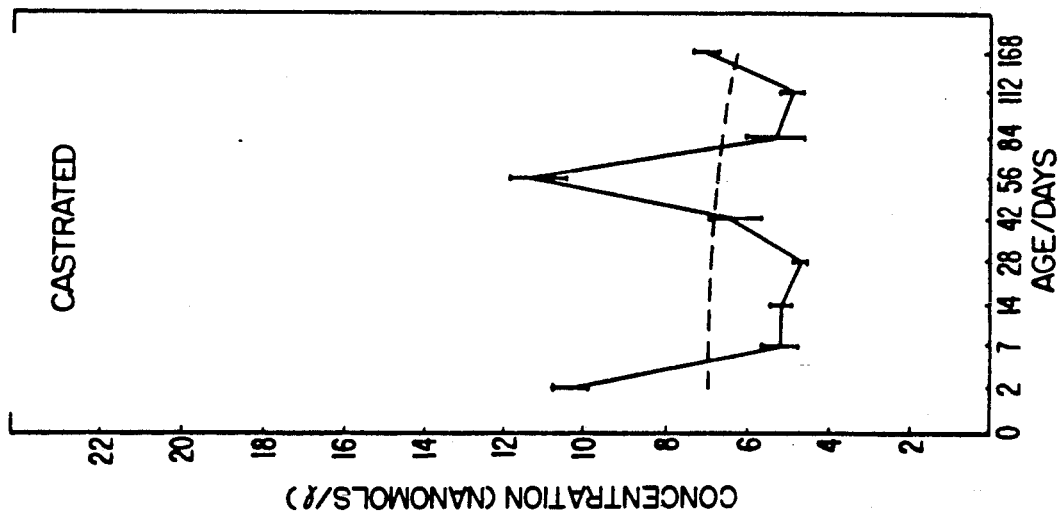
FIG. 2B CASTRATED
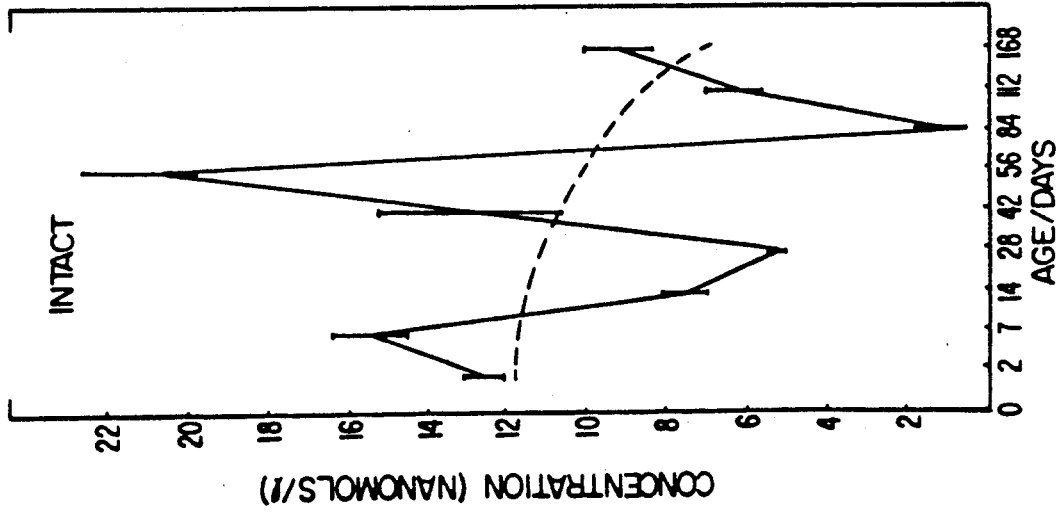
FIG. 2A INTACT

METHOD FOR PROMOTING GROWTH AND IMPROVED MEAT QUALITY IN MEAT PRODUCING ANIMALS WITH FEMALE STEROIDAL HORMONES

This application is a continuation of application Ser. No. 07/582,774 filed Sep. 14, 1990; now abandoned, which is a continuation of application Ser. No. 07/210,168, filed Jun. 21, 1988; now abandoned, which is a continuation-in-part of application Ser No. 06/696,563, filed Jan. 30, 1985, entitled Procedure for Promoting Growth in Animals; now abandoned.

TECHNICAL FIELD

This invention relates to a method of promoting the growth and increasing the food conversion efficiency of meat-producing animals in general and improving the quality of meat obtained therefrom and is concerned more particularly with the administration to a meat-producing animal, such as pigs, cattle, fish and the like, of at least one female gonadal steroidal hormone prior to its sexual maturation, and preferably at an early state of its growth, so as to retard the sexual development of the animal while simultaneously promoting its growth to a surprising degree.

BACKGROUND ART

It has long been desired to increase the rate of growth in meat-producing animals as well as to enhance the quality of the meat derived therefrom, especially as regards the proportion of lean to fat in such meat. Progress has, of course, been made to this end by the hybridization of various meat producing animals and in formulating improved feed compositions with a view to achieving an increase in the rate of growth of the animal and the efficiency of the conversion of its feed, i.e., the ratio of unit weight of meat produced per unit quantity of feed consumed, but little hope appears to exist for further major progress along these lines.

Another long-recognized approach adopted for male meat-producing mammals is castration of animals usually at an early stage in their development for the purpose of achieving a kind of feminization of the male animal while simultaneously eliminating its normal aggressive behavior and sexual activity. More recently, castration has been combined with hormone administration typically accomplished by a continuous release hormonal implant inserted, for instance, in the ear of the castrated animal at an age typically of 2-3 months. The the quantity of the hormone and the rate of its release from the implant, as determined by the composition of the implant, are so designed as to achieve a gradual and continual release of the hormone into the animal's system and so correlated with the rate of metabolism of the hormone in the animal's system that the quantity of hormone remaining in the ultimate meat obtained after slaughter was sufficiently small as to satisfy applicable government standards. While castration alone or combined with a hormone implant has some beneficial consequences on the ultimate meat production in terms of increased weight production and thus better feed efficiency, much of the improvement is in the form of increased fat, e.g., a higher ratio of fat to lean which, of course, offsets the overall improvement by reduced meat quality.

Considerable research has been done by the present applicants, their associates, and others in the field of hormones in order to acquire a better understanding of the enormously complex changes that are involved in hormone secretion in animals and the effects of such secretion in various animal species. Extensive studies have been applied to such animals such as fish, chicken, pig and ruminants such as deer. Thus, it has been described how the adenohypophyseal cells of teleost fish, chicken, rats and pigs respond to gonadal steroids administered during embryogenesis, the neonatal or "critical" period, the adult stage, and during old age. This research was done by V. R. Pantic in "Synthesis and Release of Adenohypophyseal Hormones", Plenum Press, N. Y. 1980 (M. Jutisz and K. W. McKerns, eds.) pp. 335-362. Gonadotropic cells that secrete FSH and LH were found to be suppressed, while prolactin and growth stimulating cells were increased. The effects were most pronounced during embryogenesis and the neonatal critical period. These studies were continued, with the emphasis on prolactin target cells, by V. R. Pantic, in "Regulation of Target Cell Responsiveness", Vol 2, Plenum Press, N.Y. 1984 (K. W. McKerns, A. Aakvaag and V. Hansson, eds.) pp 283-295. Further, it has been shown by F. C. Bancroft, P. R. Dobner and Li-Yuan Yu, in "Synthesis and Release of Adenohypophyseal Hormones", Plenum Press, N.Y. 1980 (M. Jutisz and K. W. McKerns, eds.) pp. 311-333;that glucocorticoids induce pregrowth hormone messenger RNA. A description has been provided how prolactin, growth hormone, and chorionic somatomammotropin are derived from a common evolutionary ancester protein. All are lactogenic and growth promoting: W. L. Miller and S. W. Mellon, in "Regulation of Gene Expression, Plenum Press, N.Y. 1983 (K. W. McKerns, ed.) pp. 177-202. During evolution the genes for these hormones migrated to separate cell types and are under complex regulatory processes.

The complexity of hormonal effects and the difficulty of predicting the consequences of the same is illustrated by the different and even opposite effects that are often obtained according to the amount and the duration of the administration of a given hormone as well as the period of such administration in the development of the animal. For example, a low-level constant administration may continually suppress a particular function; a single higher does may initially suppress that function, followed by a rebound increase. The suppression of adrenal cortex secretion by estrogen, followed by a marked rebound increase in adrenal glucocorticoid secretion has been described by K. W. McKerns in "The Regulation of Adrenal Function by Estrogens and Other Hormones", Biochemica Et Biophysica Acta, 71 (1963) 710-718.

From the information obtained during studies such as the above as well as subsequent unpublished research, it has been discovered, quite remarkably, that the administration of a female gonadal steroidal hormone to meat producing animals if applied to the animal before its sexual maturation, and preferably quite early, especially during its neonatal period, a surprising and entirely unexpected selective response is induced by which the sexual maturation of the animal, e.g., achievement of the gonadal function such as spermatogenesis in males and development of secondary sex characteristics is suppressed or retarded while the growth function and anabolic effect of the animal is enhanced and made more efficient. Those knowledgeable in endocrinology have traditionally believed that sexual maturation, e.g., spermatogenesis in the male, the development of secondary sexual characteristics, including the development of the seminal glandular system of the animal, and release of androgen and growth hormone prolactin complex to achieve a growthanabolic effect in male animals occurred together in the natural maturation of the animal. Thus, castration would obviously prevent spermatogenesis and the development of secondary sexual characteristics but with a consequential reduction in the release of androgen and its anabolic effect and the growth hormone-prolactin effect so that growth production was channeled more toward fat rather than muscle or lean meat.

In the practice of the present invention, an unexpected and surprisingly selective or differential response has been found, by which spermatogensis and secondary sexual development are temporarily suppressed or blocked while simultaneously androgen and growth hormone-prolactin production, as manifested, for example, by the level of the male gonadal hormone testosterone is not only not suppressed but remains at least comparable to, if not higher than, that taking place in similar untreated animals. As a consequence, the animal can be brought to its normal slaughter weight at a time significantly earlier than is required for untreated or intact animals or castrated animals. The conversion of the feed by the animal during the growth period up to slaughter, which is its most rapid growth period, takes place at a significantly more efficient rate, as measured in terms of unit weight of meat derived per unit weight of feed consumed. Further, the proportion of fat is reduced so that a leaner meat product having a higher ratio of lean to fat is obtained giving a significantly higher meat quality. The characteristics of the meat in other respects such as flavor, tenderness, texture and so on do not appear to be adversely affected by the practice of the present method and remain at least as acceptable as, if not better than, those of meat obtained from untreated animals, including castrates.

Additional benefits have also been observed in some species notably the pig. Sexual maturation in the male pig occurs, on the average, at around five months and is manifested by aggressive behavior and sexual activity such as fighting with other males and attempted mountings. As the secondary sexual characteristics become fully developed, the seminal system becomes operative resulting in the strong odor characteristic of boars and this strongly oderiferous seminal fluid permeates the tissue of the animal causing its meat to be tainted for most human consumption. Male pigs treated according to the present invention do not exhibit such aggressive behavior and are free from the obnoxious scent and meat flavor of untreated male pigs.

The reality of the improvements described above has been theoretically confirmed by histological testing of the treated animals compared with untreated animals. Thus, the present method has been shown to lead to induction, proliferation and increased gene expression of growth and prolactin cells in the pituitary that secrete growth hormone, growth factors and prolactin hormone. Prolactin has both a growth stimulating effect and a gonad suppressing effect. Pituitary gonadotrophs that secrete folicle stimulating hormones (FHS) and luteinizing hormones (LH) appear to be suppressed in number and function. The pro-opioidcorticotropin cells appear to be increased. Inccreased endorphins (and other opioid compounds) from these cells may have a sedative-tranquilizing effect on the animals. Increased corticotropin (ACTH) enlarges the vascular and reticular zone of the adrenal cortex and increases glucocorticoid and androgen production.

More specifically, taking the pig as an example, it was observed histologically by the light microscope and the electron microscope that growth hormone and prolactin cell types in the pig pituitary were increased, as were cells that secrete pro-ACTH-endorphin. On the other hand, gonadotropin cells that secrete FSH and LH were decreased.

DISCLOSURE OF INVENTION

Briefly, in the invention, an effective amount of at least one female gonadal steroidal compound, i.e., of the steroidal estrogen and progestagen types, is administered to meat producing animals, such as pigs, cattle, fish and other species, before the sexual maturation of the animal, and preferably at an early, and optimally very early, stage in its development, such administration in amount and duration being sufficient to repress the gonadal function of the animal during a significant portion of its growth period and being terminated so that the administered steroidal compounds are at least substantially eliminated by the natural metabolic action of the animal prior to its slaughter so that the resultant meat is essentially free of added hormones and within the acceptable limits for safe human consumption or as imposed by government regulation.

More specifically, it is preferred that a mixture of a steroidal estrogen compound and a steroidal progestagen compound be administered in which the progestagen compound considerably predominates. Such a proportionation conforms generally to the levels of these hormones occurring naturally in mammals as well as those recognized safe for administration to humans for other purposes, for example, birth control. An optimum ratio has been found to be approximately 5:1 but other ratios including equality and even an excess of the estrogen compound are possible within the broad scope of the invention. A factoral design useful in determining suitable dosage combinations for this mixture of female steroidal hormones appears below as Table 1:

TABLE 1

| Factoral Design to Establish Optimal Dose Combination for Pigs | | | |
|---|---|---|---|
| | Progesterone (mg) | | |
| Estrogen (mg) | 0 | 125 | 250 | 500 |
| | 25 | 125 | 250 | 500 |
| | 50 | 125 | 250 | 500 |
| | 100 | 125 | 250 | 500 |

In principle, all combinations within the design of Table 1 are useful, exclusive of the 0/0 combination.

Moreover, within the broad scope of the invention, either an estrogen type hormone or a progestagen type steroidal hormone can be administered exclusively, although a combination of the two is much preferred and has been found to give significantly more useful beneficial effects in the treated animals. Where a single hormone of these types is selected, the levels of administration thereof should be substantially increased, say at least doubled, over the amounts of the corresponding compound in the preferred compound in the preferred combination. Although full studies have not been carried out up to now, it is believed that progestagen will give a stronger effect over an estrogen type compound and would hence be preferred if only a single compound is employed.

It will be understood that the terms steroidal estrogen and steroidal progestagen each refer to groups of closely related compounds, there having now been developed a great variety of specific compounds or derivatives within both of these groups, as can be identified with any of the variously available pharmacological handbooks. Certain of these compounds are produced naturally in the animal and are available as extractants from natural sources. As natural compounds, they are usually accepted as safe for administration to animals and humans, within reasonable limits, without the necessity for any special approval by governmental agencies, e.g., the Food and Drug Administration, and such natural compounds are somewhat preferred for this reason. Thus, a preferred estrogen steroidal hormone is estradiol, preferably in the form of one of its pharmacologically acceptable esters, such as the dipropionate, and hydroxyprogesterone, preferably in the form of one of its pharmacologically acceptable esters, such as the caproate are among the most preferred compounds.

Many other estrogenic and progestagenic hormones are in principle applicable in the practice of this invention and broadly speaking, any one of these categories of hormones that have been established to have an estrogenic or progestagenic function so as to be useful, for example, in hormone therapy in humans or animals can be employed here from those which are already or subsequently become available in the pharmaceutical field. In other words, the present invention resides in the application of hormones known in themselves, for a specific and extraordinary function rather than in the development and perfection of new kinds of specific hormones.

The various available estrogen and progestagen compounds can be readily identified from pharmaceutical handbooks and other texts, and reference may be had to these sources for guidance in selecting a specific compound or mixture of compounds to be administered in accordance with this invention. The natural estrogens, i.e., estradiol, estrone and estriol, are identified in *Merck's Index* together with the various commonly known derivatives thereof, a particularly lengthy list of derivatives appearing in the 8th edition, 1968, of this text. Most of these derivatives are mono- or polyesters of various organic acids, of which the 3-benzoate and the dipropionate of estradiol are especially preferred. Other forms of these compounds such as their salts are also known and pharmaceutically acceptable salts where available and accepted for hormone therapy are useful in principle. An additional tabulation of estrogens and progestagens appears in the text *Essentials of Medicinal Chemistry* by Korolkovas & Burckhalter, John Wiley & Sons, copyright 1976, in Table 40.3 (pages 629–631) and 40.4 (pages 633–635). A further tabulation containing mainly synthetic progestagens can be found in the *Handbook of Chemistry and Physics*, 1975–76 edition at pages C-756–759. More complete information as to the variety, nature, properties and effects of specific members of these two groups of hormones can be found in more specialized texts, and inasmuch as resort can be had to this material for additional information, further elaboration as to the specific compounds useful here is unnecessary.

As is generally known and accepted, the various specific compounds that are available for purposes of this invention are generally similar in characteristics and behavior, differing mainly in the specific rate at which they are metabolized by the system of the animal and eliminated therefrom as well as in their rate of absorption by the body and their stability. These minor variations are of little or no consequence as regards the overall performance of these compounds in this invention.

It is well known that steroidal hormones in general are readily metabolized by the animal's system so that any excess over the natural level of the hormone in the animals (and both male and female each have significant measurable levels of both estrogen and progesterone type hormones as well as testosterone) is removed within 24–48 hours. The administration of the female gonadal hormone here must continue over a sufficient period of time during the development of the animal as to inhibit or retard its sexual maturation until after slaughter, say 30 days or so, although longer and somewhat shorter times could be utilized if desired. The application of multiple dosages of the steroid compound during this period is a workable approach but may not always be convenient. A preferred mode of administration to mammals is the hypodermic injection of the hormone in an acceptable carrier or other form which retards the release of the hormone into the animal's system. The preferred compounds designated above have little solubility in water but are sufficiently soluble or dispersable in oil vehicles as are conventional and typically used for pharmacological compositions designed for injection, of which vegetable oils, such as olive oil, are preferable, although other pharmacologically useful oil vehicles should be acceptable in principle. The combination of the oil vehicle and the hormone combines to achieve a sufficiently slow release of the hormone into the animal's system for present purposes covering a period of considerable days and even up to about 30 days especially if the injection is accomplished subdermally to produce a pocket of the hormone in oily vehicle immediately below the skin of the animal which is gradually absorbed. Intramuscular injection is also possible but usually entails an increased rate of absorption as is known. The amount of the mixture injected may vary but a few ml, say 2 ml, is ordinarily sufficient, depending of course on the concentration of the hormone.

In many instances, a single dosage at an effective level of the female gonadal hormone will suffice in the present practice; however, as mentioned, multiple dosages may be utilized especially for larger animals, or multiple dosages at reduced levels at intervals of several days, perhaps 2–3 days to 7 days, or longer in some cases, could be substituted if preferable. The site of the injection can be varied to suit an individual preference but the inguinal region or groin has been found entirely satisfactory in the case of pigs.

Derivatives of the steroidal hormones in question have been produced which exhibit increased water solubility and especially for such compounds, oral administration is an alternative route of administration, and in any case, oral administration is necessary for some food producing species, such as fish and shellfish that obviously cannot be inoculated on any practical basis. Alternatively, since even the poorly water soluble steroidal hormones usually have some small degree of water solubility, the amount of the administered compound could be increased so as to achieve a level of assimilated hormone that is consistent with the active levels described above, the unabsorbed excess of the hormone simply being eliminated through the animal's digestive tract.

Where oral administration is desired or necessary, the hormone can be incorporated in the feed of the animal species at a very low level, say a fraction of a percent, e.g. 0.5, up to 1–2% by weight, as to be consistent with thorough mixing and safe application by avoiding pockets or localized areas of excessively concentrated material. Thus, food pellets containing the hormone or pelletized hormones mixed with a greatly predominant amount of granular feed could be used, being made available to the animal during the administration period for a period of some days, dependent upon the particular species being treated. Alternatively, most mammalian species, especially cattle and sheep are ordinarily given so-called feed supplements containing enhanced levels of protein, minerals, vitamins and the like and small levels of the active hormone could be incorporated into such supplements, being made available to the animals separately from their standard feed. In this fashion somewhat better control over the uptake of the hormone by individual animals can be exercised than if the active hormone is applied via the general feed mixture.

There are also now available hormone derivatives in which an estrogen function and a progestagen function are combined into the molecule of a single compound. Standardized texts have been developed for measuring the effective level of these respective functions and such measured effective levels can be equated with the effective quantity of the individual hormones of a combination for purposes of administration. That is to say, if such a "composite" compound should exhibit comparable functional activity for each of the estrogen and progestagen functions corresponding to the relative proportions of the separate estrogen and progestagen compounds referred to above, then such a combined compound could be substituted in entirety. Alternatively, if the estrogen function or the progestagen function of a combined compound were less or greater as the case may be, than the desired relative proportions as determined for the separate compounds, then such a composite compound could be supplemented with the amount of additional estrogen or progestagen compound as needed to achieve the desired relationship of the two hormone functions.

As indicated above, inasmuch as an essential result of the present concept is the suppression of the sexual maturation of the animal, the administration must obviously be initiated before sexual maturation has taken place. Although, broadly speaking, sexual maturation is a gradual lengthy process, its culmination in the sense of the capacity to produce young either as a male or female is for a given animal, as in humans, a fairly well defined event in time, although the point in time of that event will vary considerably between individual animals of the same species. Full sexual maturation can be identified scientifically by histological examination under, for example, an electron microscope of the brain cells and neurons of the animal to ascertain whether or not fully mature cell differentiation in critical areas of the brain, notably the pituitary, has already occurred. A more empirical but nonetheless useful standard can be followed based on common experience and observation of the animals in question inasmuch as sexual maturity is, as already mentioned, typically manifested by readily perceptible sexual activity and aggressive behavior especially on the part of males, including fighting and attempted mountings. This usually occurs in the pig at around 4–5 months, and thus administration in this invention should be begun well before that time.

The closer the administration is begun to the point of full sexual maturation, the less the improvement that can be achieved by the practice of this method. Consequently, administration is strongly preferred to be initiated quite early and in any case long prior to full brain cell differentiation and sexual maturation. By beginning early in the life of the animal, brain cell differentiation in the critical areas of sexual development and growth are at a minimum and thus the remarkable effects of the present concept on brain cell development are maximized. The optimal timing for mammals is during their so-called neonatal period, that is during the few days following their birth. In the pig, the neonatal period corresponds to days 1–7 after birth and administration during this period appears to be ideal for purposes of this invention. Indeed, administration at day 1 for pigs is particularly preferred since this is the normal occasion for castration of male piglets in the practice of the age-old castration technique, for the administration of iron and/or other injections, and for the clipping of the needle teeth of the piglets so as to minimize nursing discomfort to the brood sows. Thus, a single injection on day 1–3 of the administered hormone, e.g., a mixture of a natural estradiol hormone and a progesterone compound in the proportions described above, say 50 and 250 mg, respectively, in a vegetable oil vehicle, has been itself to give eminently satisfactory results in achieving the objects of the present invention. If preferred, a second dose at equal or reduced levels could be added at about day 7 particularly if the initial dose were reduced accordingly. The injection of the just identified mixture in six-week old piglets, however, still induced Leydig cell (testis) hyperplasia and hypertrophy with a ninefold increase in serum testosterone, indicating the inducement of a marked anabolic effect in these piglets, although administration at this time was less effective in increasing prolactin-growth hormone.

As will be observed from later data, the very rapid weight gain that occurs in mammals during their initial growth phase, e.g., in piglets up until about day 120 following a single injection at day 1–3, falls rapidly and in order to sustain an increased weight gain after this time, an additional injection prior to the end of this period, e.g. prior to day 100 for pigs, should prove advantageous, subject to the requirement that the added hormone be eliminated from the animal's system sufficiently early prior to slaughter.

The levels of administration of the female steroidal hormone do not appear critical and can vary considerably. While the hormones in question presumably have toxic limits like virtually all other medicinal compounds, such limits if they are known are far greater than even the maximum levels that need be applied in this invention, and toxicity thus is not a matter of concern here.

An evaluation of the appropriate level of administration can be carried out scientifically by histological scrutiny of the brain cells of the animals being treated compared with comparable untreated animals for the actual detection of significant alterations in the rate of development of the sexually-related cell functions in the brain. However, a less rigorous but practically useful evaluation is possible by a simple observation of the animals since when the female hormone is being applied at an acceptable level, the male animals exhibit a small but perceptible amount of nipple enlargement or swelling. Hence, if such swelling or enlargement is taking place, this indicates administration of the hormone at an effective level. Obviously, gross or massive nipple and breast enlargement in the treated male animals is not desirable and in the unlikely event that such were observed, the levels of hormones being administered would be deemed to be excessively high and should be reduced in future treatments.

In the case of pigs, administration of a mixture of an estradiol and progesterone in amounts of 25 and 125 mg, respectively, during the neonatal period was found to be somewhat less effective than the preferred dosage levels of 50 and 250 mg. On the other hand, if the preferred dosage levels are doubled, e.g., to 100 and 500 mg, respectively, the results were found to be slightly better when administered during the neonatal period than the preferred dosage but not proportionately better and not sufficiently better in view of the doubled dosage of the hormones.

When the hormone mixture is administered in an oily vehicle, the levels in the blood of the administered hormones, starting from an elevated level upon injection, drop gradually until at the 28–30 day age, where injection takes place on the first or second day, the levels have decreased to the normal blood levels for the hormones in question in the animal. Inasmuch as the animal is normally slaughered well after this time, slaugher in the case of pigs occurring when the pig reaches a weight of about 100–110 kg (or about 220–240 pounds) which is reached when the pig is about 5–6 months old, this natural clearing effect of the hormone from the animal's system means that the hormone is completely eliminated well before slaughter. Elimination of the administered hormone, i.e., the excess above normal blood levels, not later than 60 days prior to slaughter is considered entirely safe, although it is believed that elimination not later than 30 days prior to slaughter will prove equally safe and acceptable. Given these acceptable time limitations, the administration can obviously continue past the one month period in pigs, for example, up to the point where clearance occurs at the appointed time prior to slaughter. Although the usual pharmacologically inert carriers are entirely suitable, specialized measures could be adopted for achieving a sustained release of the active hormone if preferred. Inert polymeric matrices, such as that sold under the tradename "Silastic" by Dow Chemical have been developed for this kind of release and could be utilized here along with similar developments.

Compared to untreated intact animals and untreated castrated animals, the treated animals are found to be bigger and longer in size, the proportion of lean meat to fat has been significantly increased, slaughter weight is achieved within a significantly shortened period of time, e.g., about 15–20 days in the case of pigs, and the efficiency of the animal's conversion of the feed as expressed in terms of unit weight of meat product per unit weight of feed consumed is significantly increased. Due to the significant acceleration of the feeding cycle, whereby the pig, for example, reaches a market weight of about 100 kg in about 165–170 days, compared to about 185 days for both intact and castrated pigs, the overall production cycle at a mass production facility can be definitely greater.

Up to now, no adverse effects have been noticed in the practice of the invention. Although spermatogenesis is inhibited as is the development of secondary sexual characteristics beyond the normal slaughter time, if the male animals should not be slaughtered, they eventually exhibit normal sexual development and activity although at a somewhat later time than untreated animals. The method of the invention does not cause any ultimate deformity or diminution in the sexual function of the animal, testicular development being normal with only spermatogenesis being temporarily delayed.

While the present method is aimed primarily in the case of mammals at the male animal, some modest potential exists for extending its improvement to female animals. The desirability or benefit of administration to females is inherently less than in the case of males inasmuch as the meat of female animals is already more desirable and preferred than is the meat of males. The achievement of any androgen effects in females is not possible by the present method although some improvement in the growth hormone effect should be realizable perhaps at about 5–10% better growth rate than the untreated females. Similarly, some improvement in the lean meat to fat ratio would be expected. The timing of the administration and other conditions would follow along as for the males.

Hormone implants on castrated animals are employed with cattle which are normally castrated at three months or so and the continuous release has a strong feminizing effect distinct from the growth stimulation of the invention.

In the case of cattle, the neonatal period extends from day 1 through about day 21 and administration preferably takes place during this period and ideally quite early in this period, say day 1 or day 2 as with pigs, although delays beyond this date are readily possible. The level of administration for larger animals does not increase proportionately with increasing body weight of the animal at the time of administration, although some increase in the absolute amount of the administered hormone is indicated for larger animals. Thus, for a new born calf weighing about 36 kg, the level of the administered hormone should perhaps be twice that employed for new born piglets weighing about 1.1–1.2 kg, and the duration of administration for cattle should be around about two months or so but can continue longer in view of the considerably greater age of cattle for slaughter. Thus, beef cattle are normally slaughtered at an age greater than one year, say about 14 months, and the maximum conceivable duration of administration is such as to be cleared from the animal's system about 30–60 days prior to slaughter. The latest time for administration to cattle would be at around four months of date but earlier times are much better. Multiple dosages might be more convenient with cattle, say three dosages, one at the preferred level of the mixture on day 1 or 2 and the next at a total of say 300 mg approximately two weeks later, and a third at 1–2 months of age at the 300 mg level. In addition to ordinary beef cattle, other livestock such as veal and so-called "baby beef" can likewise be treated.

The principle of the invention is applicable to fish and shellfish, and the results of the practice of the invention are in some respects even more extraordinary for fish than for mammals. Fish at birth or hatching are not sexually differentiated in contrast to mammals where the sex of a given animal can be readily discerned at birth (sexual differentiation of mammals generally occurring during gestation). Similarly, fish have a considerably less highly developed brain and endocrine system than do mammals at the time of birth so that the entirety of the hatch of young fish can respond to the present method without the male/female differences noted above in mammals. In fact, whereas fish eventually develop into males and females at about a 50:50 ratio under normal growing conditions, treatment of the fish by the present invention causes a substantial shift toward the development of females to give a male to female ratio of about 20–30:80–70. The disproportionate increase in the ratio of female fish is advantageous since female fish have better growth characteristics than males. It is notable also that the invention results in an increased number of hermaphrodite and sterile fish which is advantageous from the standpoint of meat production since it avoids the energy consumed by the sexual cycle, i.e., for egg production, which is considered wasted for purposes of meat production. The sexual maturation of the fish is likewise delayed so that they reach marketable weight earlier and can be harvested before breeding takes place.

Newly hatched fingerlings are born with an attached yolk sac which is consumed by the fingerlings during about the first 3–4 months of their existence dependent upon such factors as water temperature and amount of available light so that the fingerlings do not actually begin feeding in the sense of consuming externally supplied food until 3–4 months of age. Obviously, the hormone of the invention cannot be administered to fish until after they have begun to feed and preferably the administration is begun at their first feeding.

The hormone is supplied to the fish via their food, being incorporated into the usual food pellets or granules at a level of about 0.5–2.0% by weight. The feeding can be extended for about 5–7 days and longer if desired, but 5–7 days has been found entirely sufficient and further administration of the hormone seems to produce no corresponding increase. While the rate of growth for fish is affected by external conditions such as water temperature and the amount of available light, in general fish such as rainbow trout are ready to be harvested and marketed at about one and one-half years age counting an initial three months period for assimilation of the yolk sac, or say about one to one and one-quarter years after the first feeding. By this time the administered hormone is fully cleared from the fish's system. The period of administration can, therefore, certainly be extended safely but availability of the hormone at the usual feeding intervals during the first week to two weeks after first feeding of the fish has been found entirely sufficient to produce significantly desirable results. Excess or over-feeding of the hormone-containing feed should be avoided during this period.

Although the mixture of an estrogen compound and a progestagen compound as preferred for mammals can likewise be utilized in the case of fish, it is preferred for the latter to administer an estrogen compound alone, selected from those available to the art. The inclusion of any progestagen compound does not appear to significantly influence the response of fish to the present method. Both cold and warm water fish respond to the invention, including salmon, rainbow trout, carp and others currently being cultivated.

The invention is also deemed to be applicable to various shellfish including shrimp, lobster, crayfish, oysters, mussels and the like, and in general, the treatment would follow the same pattern for these species as for fish, the hormone being administered early in the feeding cycle of the species via the feed that is supplied thereto following principles that are now well developed for the forming of such species.

Turning now to poultry, chicks are differentiated sexually at birth and have a higher level of brain and endocrine development than do fish, but nevertheless, the present method will have beneficial effects on both male and female chickens. The hatch time for chicken eggs is approximately 30 days, and while it is technically possible to inject the chicken embryo with the hormone within the egg, this practice is contraindicated here due to the potential for causing increased abnormalities in the chicks after hatching. The hormone is applied to chickens via their feed being incorporated into the feed at a level of say about 0.5–2% by weight. Inasmuch as chickens are already bred to maximize feed efficiency, the effect of the invention on chickens is not anticipated to be as high as for mammals, fish and the like. The response of chickens more closely parallels that of mammals than fish in that the invention causes no alteration in the normal male/female ratio. A mixture of an estrogen and a progestagen compound is preferred for administration to poultry but estrogen alone could be substituted with less beneficial results. Poultry, of course, includes turkeys, Cornish game hens and other commercially produced fowl.

EXAMPLE I 150 male piglets of a strain of Swedish Landrace were divided into groups of 50 and were either castrated, left intact or given a single injection with the compound mixture under the skin in the scrotal area during the neonatal period, specifically on day 1 or 2 after birth. The injected composition was a mixture of 50 mg of estradiol dipropionate and 250 mg of progesterone caproate, i.e., 17α-hydroxyprogesterone caproate, dissolved or dispersed in olive oil as a vehicle or carrier. Prior to weaning, animals were given a pre-weaning feed, and after weaning a post-weaning feed, followed by a growth and finally a finishing feed, all feed mixtures being regular formations of generally known types. The pigs were kept in semi-confinement, ten pigs in an open cage until an average weight of 50 kg was achieved, and then 20–22 pigs in a much larger open cage until market weight of approximately 100 kg had been reached. Animals were sheltered and had free access to water and feed. Every fourteen days the animals in all groups were weighed, the daily food consumption, and the food consumed per kg of body weight gain were calculated. Animals were sacrificed at intervals and meat quality observed.

In Table 2 the average food consumption per day is given. Table 3 shows the average food uptake or conversion per kg of weight gain, which is a measure of feed efficiency. The feed efficiency of the treated animals was considerably better than the castrated or intact animals at almost every test interval.

TABLE 2

| | Average Food Consumption in Kg per Feeding Day of Male Landrace Pigs | | | | | | | | | |
|---|---|---|---|---|---|---|---|---|---|---|
| | Day | | | | | | | | | |
| Group | 63 | 77 | 91 | 105 | 119 | 133 | 147 | 161 | 175 | 190 |
| Castrated | 0.88 | 1.22 | 1.50 | 1.81 | 2.10 | 2.32 | 2.50 | 2.50 | 2.50 | 2.04 |

TABLE 2-continued

Average Food Consumption in Kg per Feeding Day of Male Landrace Pigs

| Group | Day | | | | | | | | | |
|---|---|---|---|---|---|---|---|---|---|---|
| | 63 | 77 | 91 | 105 | 119 | 133 | 147 | 161 | 175 | 190 |
| Intact | 1.00 | 1.26 | 1.40 | 1.25 | 2.09 | 2.63 | 2.41 | 2.63 | 2.19 | 2.11 |
| Treated | 0.62 | 1.20 | 1.60 | 2.09 | 1.83 | 1.78 | 2.00 | 2.57 | 2.14 | 2.00 |

TABLE 3

Average Food Consumption in Kg per Kg Weight Gain of Male Landrace Pigs

| Group | Day | | | | | | | | |
|---|---|---|---|---|---|---|---|---|---|
| | 77 | 91 | 105 | 119 | 133 | 147 | 161 | 175 | 190 |
| Castrated | 2.25 | 2.96 | 3.13 | 3.40 | 3.99 | 3.42 | 3.68 | 3.52 | 4.59 |
| Intact | 2.77 | 2.89 | 2.33 | 3.07 | 3.58 | 3.16 | 4.21 | 3.70 | 3.61 |
| Treated | 2.22 | 2.60 | 2.77 | 2.94 | 3.21 | 2.62 | 3.61 | 3.88 | 3.16 |

Differences between groups from birth to 49 days are minimal. From 49 to 105 days food consumption of treated pigs was about the same as the intact control group. Daily weight gain of treated pigs was markedly higher throughout this period (e.g. on day 63 the 43 lb treated pigs had gained 475 grams [10.5 lbs] over the previous 14 days, with a feed conversion of 1.3, compared to the 33 lb castrate which gained 380 grams [8.4 lbs]. On day 105 treated pigs. gained over the previous 14 days 775 grams [17 lbs] and castrates 590 grams for a 35% better conversion for the treated pigs).

From day 119 to 163 treated pigs were gaining slightly more than castrates on considerably less feed. Treated were 22 lbs heavier than castrates throughout the period 100-179 days with a much higher proportion of meat to fat (44% less back fat).

From 163 to 190 days feed consumed and daily gain dropped in treated and castrates, although feed efficiency was still much better in treated. It should be noted that on day 161 treated pigs are at or near U.S. market weight (180 lbs for U.S. No. 1 Grade). Feed efficiency is 3.1. Castrates average 158 lbs and it would be 178 days before they reach 180 lbs with a feed efficiency at that time of 4.5. That is, another 15-16 days of feeding at efficiencies at 4.0 to 4.5, approximately 100 lbs of feed. The data is summarized in Table 4 below.

TABLE 4

Food Conversion and Body Weight of Landrace Pigs

| Day | | Food Efficiency | Body Weight |
|---|---|---|---|
| 63 | treated | 1.3 | 19 kg (42 lbs) |
| 49 | castrate | 1.7 | 10 kg (22 lbs) |
| 105 | treated | 2.5 | 45 kg (99 lbs) |
| 105 | castrate | 3.2 | 33 kg (73 lbs) |
| 147 | treated | 2.6 | 72 kg (158 lbs) |
| 147 | castrate | 3.4 | 62 kg (136 lbs) |
| 161 | treated | 3.1 | 82 kg (180 lbs) |
| 161 | castrate | 3.6 | 72 kg (158 lbs) |
| 179 | treated | 3.9 | 100 kg (220 lbs) |

TABLE 4-continued

Food Conversion and Body Weight of Landrace Pigs

| Day | | Food Efficiency | Body Weight |
|---|---|---|---|
| 179 | castrate | 4.6 | 90 kg (198 lbs) |

Two main effects of the treated pigs compared to castrates can be seen. First, there is a very marked increase in daily body weight gain for about the same feed consumed up to approximately day 119 (53kg or 115 lbs). This is at a maximum from day 63 (15%) to day 105 (40%). Secondly, a marked decrease in food consumption occurs from day 119 to day 161 with a slight increase in daily weight gain compared to castrates. This is better than a 30% increase in feed efficiency.

EXAMPLE II

In another experiment 150 male Landrace-Yorkshire pigs were divided into groups of 50, 50 of which were given 50 mg of estradiol benzoate, i.e., the 3-benzoate compound plus 250 mg of progesterone caproate subcutaneously in the inguinal region on day 1, 50 were castrated at the same time, and 50 left intact, and the weight gain and feed consumption of the several groups was measured.

Table 5 shows the average body weight at the stated interval plotted against age in days for the intact, castrated and treated male pigs. The treated pigs were considerably heavier than the other two groups throughout the test period. The treated animals reached their market weight of 100 kg in 166 days, which was 20 days sooner than the other two groups.

TABLE 5

Average Body Weight of Male Landrace-Yorkshire Pigs (Kg)

| Group | Day | | | | | | | | | |
|---|---|---|---|---|---|---|---|---|---|---|
| | 60 | 74 | 88 | 102 | 116 | 130 | 144 | 158 | 172 | 186 |
| Castrated | 19.26 | 25.56 | 37.86 | 46.80 | 57.46 | 68.26 | 76.73 | 86.40 | 93.33 | 100.50 |
| Intact | 19.20 | 27.33 | 35.53 | 45.86 | 57.73 | 69.66 | 77.20 | 85.26 | 91.80 | 98.81 |
| Treated | 20.35 | 30.20 | 40.40 | 52.00 | 64.20 | 77.00 | 87.10 | 96.60 | 100.70 | — |

Treated male pigs reached market weight (100 kg) at 166 days, 20 days earlier than castrated or intact.

Table 6 below shows the average food consumption in kg for the three groups at various time intervals throughout the growth cycle. The treated hybrid pigs consumed slightly more feed per day than the other two groups, but with a considerably greater weight increase. In addition, they reached market weight much earlier. This means a considerable saving in feed, since the final growth phase before slaughter is the one with the poorest feed efficiency. The average food uptake or conversion per kilogram of weight fain (feed efficiency) is shown in Table 7.

TABLE 6

Average Food Consumption in Kg for Male Landrace-Yorkshire Pigs

| Group | Day | | | | | | | | |
|---|---|---|---|---|---|---|---|---|---|
| | 74 | 80 | 102 | 116 | 130 | 144 | 158 | 172 | 186 |
| Cas- | 1.71 | 1.90 | 1.71 | 2.66 | 2.66 | 2.66 | 2.47 | 2.22 | 2.38 |

TABLE 6-continued

Average Food Consumption in Kg for Male Landrace-Yorkshire Pigs

| Group | Day | | | | | | | | |
|---|---|---|---|---|---|---|---|---|---|
| | 74 | 80 | 102 | 116 | 130 | 144 | 158 | 172 | 186 |
| trated | | | | | | | | | |
| Intact | 1.80 | 1.71 | 1.52 | 2.47 | 2.47 | 2.28 | 2.47 | 2.25 | 2.33 |
| Treated | 1.75 | 2.00 | 2.00 | 2.85 | 2.28 | 2.85 | 2.85 | 2.00 | — |

TABLE 7

Average Food Consumption per Kg Gain of Male Landrace-Yorkshire Pigs

| Group | Day | | | | | | | | |
|---|---|---|---|---|---|---|---|---|---|
| | 74 | 88 | 104 | 116 | 130 | 144 | 158 | 172 | 186 |
| Castrated | 3.28 | 2.35 | 2.68 | 3.50 | 3.45 | 4.40 | 3.58 | 4.23 | 3.60 |
| Intact | 3.15 | 2.89 | 2.06 | 2.92 | 2.90 | 4.24 | 4.29 | 4.48 | 3.18 |
| Treated | 2.48 | 2.74 | 2.41 | 3.27 | 2.50 | 2.96 | 4.21 | 3.90 | — |

Table 8 below sets forth a comparison of the feed efficiencies obtained in this example in three ways during three growth phases; namely, the actual average feed consumption per kg weight gain during that phase, the relative consumption (Index) taking the consumption of the castrated animals as the base (Index value=100), and the percentage change from the base. The first phase, from 20-50 kg of live weight, represents the post-weaning growth phase of pigs on a high protein diet. In this phase, it can be seen that the treated animals have an actual feed efficiency of 2.86, compared with 3.00 for the intact, and 3.39 for the castrated animals. During this phase, the treated animals have a 15.64% higher feed efficiency compared with the castrated and about 4% higher than the intact animals. In the next phase of 50-100 kg, or the so-called finishing phase, the actual feed efficiency of the treated animals is 3.27 compared with 3.62 for the intact and 3.73 for the castrated. Probably the most important comparison is the overal feed efficiency from weaning to market weight, i.e., over the full range of 20-100 kg. Here, the treated animals show an overall actual average feed efficiency of 3.08 compared with 3.32 for intact, and 3.57 for castrated pigs. In addition, the treated reach market weight of 100 kg in a considerably shorter time. This not only means an additional feed saving but a saving in labor costs, heating and other expenses in producing the animals. More animals can thus be brought to market since it becomes possible to have more production cycles from weaning to slaughter per year for a given size facility.

TABLE 8

Comparison of Feed Efficiency per Growth Phase - Kg Feed Consumed/Kg Weight Gain

| Phase | Castrated | Intact | Treated |
|---|---|---|---|
| A. Post-Weaning- 20-50 kg | | | |
| Av. Value | 3.39 | 3.00 | 2.86 |
| Index | 100 | 88.49 | 84.36 |
| % Change | — | −11.51 | −15.64 |
| B. Finishing- 50-100 kg | | | |
| Av. Value | 3.73 | 3.62 | 3.27 |
| Index | 100 | 97.05 | 87.66 |
| % Change | — | −2.95 | −12.34 |
| C. Overall- 20-100 kg | | | |

TABLE 8-continued

Comparison of Feed Efficiency per Growth Phase - Kg Feed Consumed/Kg Weight Gain

| Phase | Castrated | Intact | Treated |
|---|---|---|---|
| Av. Value | 3.57 | 3.32 | 3.08 |
| Index | 100 | 92.99 | 86.27 |
| % Change | — | −7.01 | −13.73 |

EXAMPLE III

The time required for the administered female gonadal steroidal compounds to become cleared or dissipated from the system of the animal is conveyed graphically in FIGS. 1A, 1B, 1C, 2A, 2B, 2C, 3A, 3B, and 3C.

BRIEF DESCRIPTION OF THE DRAWINGS

FIGS. 1A, 1B and 1C are a comparative group of plots of the level of estradiol in the blood serum of the animal versus the age of the animals during the experiment for each of intact animals, castrated animals and animals treated in accordance with the invention, the regression or trend line of each of the graphs being shown in broken lines;

FIGS. 2A, 2B, and 2C are a similar group of graphs for serum concentration of progesterone.

Figure 3A:
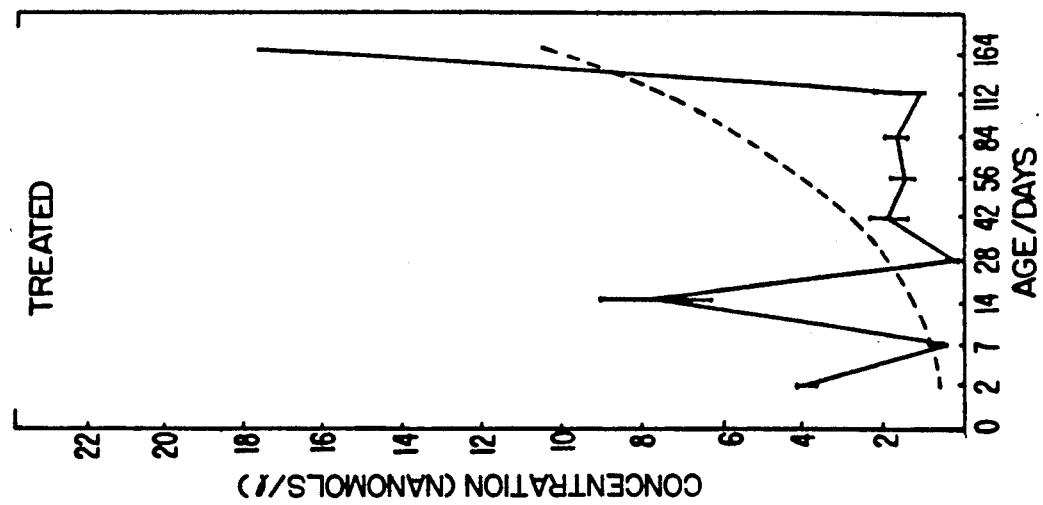
FIGS. 3A, 3B, and 3C are a similar group of plots for the serum concentration of testosterone in the various groups of animals.

In order to determine the serum levels of the hormones, estradiol, progesterone, and testosterone in animals treated in accordance with the invention in comparison to similar animals both intact and castrated, the blood serum for groups of each of these animals was analyzed for the content therein of the hormones in question by means of known radioimmunoassay techniques at intervals following the administration by injection into the treated animals and the results of these analyses are set forth graphically in the drawings. The injection composition consisted of the preferred combination of 50 mg estradiol and 250 mg of progesterone dissolved or dispersed within olive oil as a carrier, the administration being applied at day 1. The variation in the analyzed values of the respective hormones at each time of measurement is indicated in the graphs by solid vertical bars.

Figure 3B:
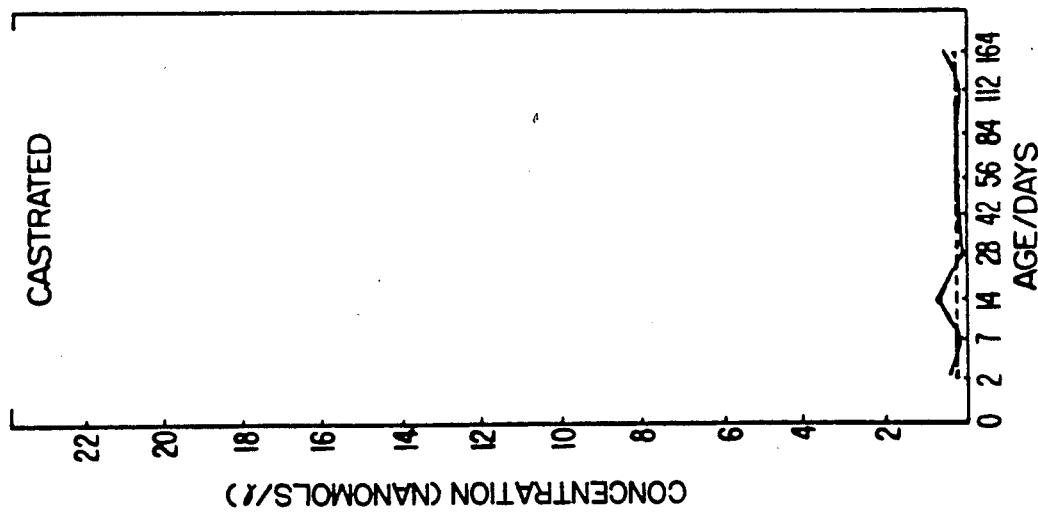
Figure 3C:
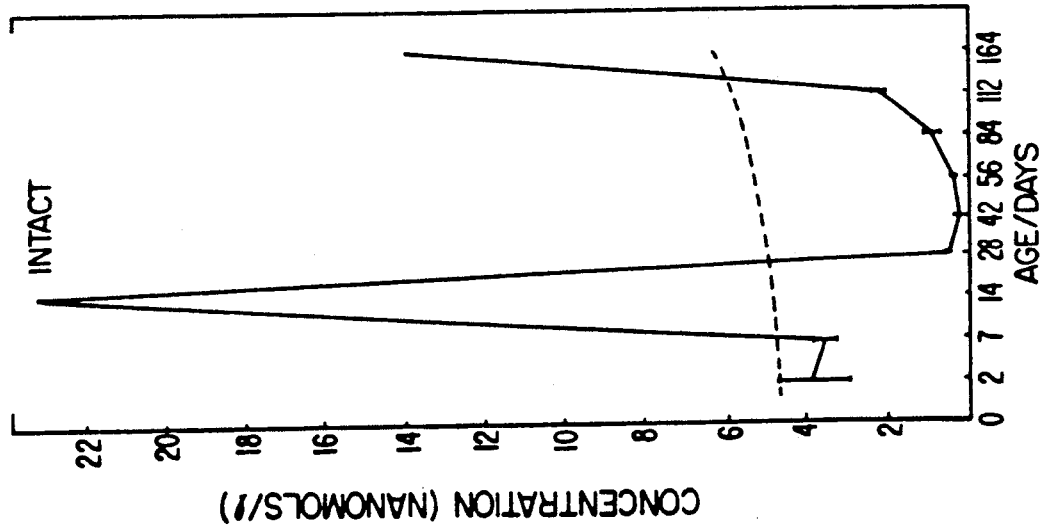

As is seen from FIG. 1A, the subcutaneous dose of estradiol in oil is cleared by 28 days, reaching by that time a basal level compared with the castrate and intact animals. FIG. 2A demonstrates that the progesterone levels in the treated animals likewise come to the same levels as the intact animals by day 28. The intact animals exhibit a secondary increase that represents an endogenous secretion of progesterone from the tests, and to a lesser extent from the adrenals, from day 28 to day 84 with a peak at day 56. Both the treated and the castrated animals in this time period have a much smaller rise in endogenous progesterone, coming entirely from the adrenal cortex in the case of castrated, and mostly from the adrenal cortex in the case of the treated animals. FIGS. 3A, 3B and 3C show the endogenous levels of androgen expressed as testosterone, in the three groups of animals. This is testosterone from the testis and, as would be expected, in the castrated animals is almost zero. The treated animals show a first peak rise in testosterone beginning at day 7 similar to the intact animals but to a lower level. Interestingly enough, the secondary phase which shows an increase in testosterone after day 28, as measured by blood levels, is greatest in the treated animals. The dotted linear regression or trend line in the treated animals shows this increase quite clearly. This represents the induced anabolic effect of the inventive treatment and is part of the improved growth effect thereof.

EXAMPLE IV

This example reveals the effect of the induction of increased growth hormones and anabolic hormones in animals treated in accordance with the invention on meat quality as determined by the ratio of lean meat to fat. Carcasses obtained from the various groups of animals corresponding to the experiments described above are evaluated on the slaughter line at the end of the experiment. The average thickness of back fat on split carcasses was 56 mm for castrate, 48 mm for intact and 39 mm for treated animals. The average back fat then, was 43.6% thicker in castrated animals compared with those treated according to the invention and 23% thicker in intact animals than in treated animals. Similar reductions in fat in treated animals were obtained in other meat cuts such as last rib cuts, bellies and hams.

EXAMPLE V

This example illustrates the application of the invention to fish, specifically rainbow trout (Salmo gairdneri) as well as the influence of different growing conditions, especially temperature and light, on the response of the fish to the instant treatment.

These experiments were carried out with many thousand of the rainbow trout at two different fish farm locations; namely, fish farm "Z" where the average water temperature was cooler in the range of about 8°–13° C. and the number of light days was fewer, and fish farm "S" where the water temperature was somewhat higher in the range of about 10°–13° C. and the number of light days was greater. The fish in the experiment at each location were separated into two groups, the first group being fed with the usual pelletized feed or "bricket" and the other were fed the same feed on which estradiol benzoate was incorporated at a concentration of 0.5% by weight and given to the fish for four consecutive days, beginning with the first feeding of the fish at an age of four months, after which the treated and untreated fish were supplied with the same feed on the same basis. These experiments were terminted when the fish reached their consumption or marketing weight which occurred at the age of 17 months for the fish at the warmer location and at the age of 20 months for the fish in the colder location.

At intervals during these feeding experiments, the fish were evaluated as to weight, and this data is summarized in the following table which is divided into two parts corresponding to the different locations.

TABLE 9A

Fishfarm "Z" - Water temperature = 8–13° C.

| Average Weight in Grams | | |
|---|---|---|
| Control | Treated | Age in Months |
| 1.85 | 1.85 | 4 |
| 6.4 | 7.1 | 5 |
| 15.0 | 16.1 | 6 |
| 24.0 | 24.0 | 7 |
| 32.0 | 35.0 | 8 |
| 38.0 | 45.0 | 9 |
| 44.0 | 51.0 | 10 |
| 52.0 | 59.0 | 11 |
| 63.0 | 74.0 | 12 |

TABLE 9A-continued

Fishfarm "Z" - Water temperature = 8–13° C.

| Average Weight in Grams | | |
|---|---|---|
| Control | Treated | Age in Months |
| 75.0 | 91.0 | 13 |
| 85.0 | 99.0 | 14 |
| 98.0 | 115.0 | 15 |
| 118.0 | 135.0 | 16 |
| 131.0 | 156.0 | 17 |
| 148.0 | 183.0 | 18 |
| 178.0 | 208.0 | 19 |
| 190.0 | 227.0 | 20 |

TABLE 9B

Fishfarm "S" - Water temperature = 10–13° C.

| Average Weight in Grams | | |
|---|---|---|
| Control | Treated | Age in Months |
| 1.85 | 1.85 | 4 |
| 6.30 | 6.50 | 5 |
| 14.50 | 15.0 | 6 |
| 21.0 | 29.5 | 7 |
| 28.5 | 38.0 | 8 |
| 39.0 | 49.0 | 9 |
| 44.0 | 61.0 | 10 |
| 55.0 | 72.0 | 11 |
| 68.0 | 105.0 | 12 |
| 94.0 | 139.0 | 13 |
| 120.0 | 161.0 | 14 |
| 148.0 | 181.0 | 15 |
| 172.0 | 196.0 | 16 |
| 204.0 | 249.0 | 17 |

It will be observed from the above tabulations that the weight of the treated fish was consistently higher throughout the growth period of the fish and was substantially greater than that of the untreated or control fish at the end of both of these experiments, such increase being over and above the differences in weight attributable to the more favorable growing conditions at farm "S".

We claim:

1. The method for treating sexually intact meat-producing domestic non-ruminant animals, to improve the yield and increase the proportion of lean to fat meat obtained therefrom when the animal is slaughtered after achieving a desired body weight, which comprises the step of non-implantatively administering to the animal to be treated at a time during substantially its neonatal stage at least one dosage of a combination consisting essentially of a pharmacologically acceptable estradiol ester and a pharmacologically acceptable progesterone ester in which the weight of said progesterone ester exceeds that of said estradiol ester, in an amount which is sufficient to produce in the animal an essentially immediate, temporary substantial increase in the level of each of said estradiol ester and said progesterone ester in the animal's system, such dosage being effective to delay sexual maturation of the animal so that sexual maturation does not occur prior to the date of slaughter of the animal while its primary sexual development and growth function remain substantially unimpaired, the duration of said increase being sufficiently short relative to the interval between the time of administration and the date of slaughter that said animal is at least substantially free of any residual amount of the thus-administered estradiol ester and progesterone ester at the time of slaughter.

2. The method of claim 1 herein said combination is a mixture of said estradiol ester and said progesterone ester.

3. The method of claim 1 wherein said progesterone ester is administered in substantially greater amounts than said estradiol ester.

4. The method of claim 3 wherein said progesterone ester is administered in an amount about five times greater than the amount of said estradiol ester.

5. The method of claim 1 wherein said combination is administered to uncastrated male animals.

6. The method of claim 1 wherein said estradiol ester and progesterone ester are administered to said animals by injection of a solution of dispersion thereof in in a pharmacological acceptable liquid vehicle.

7. The method of claim 1 wherein the amount of such dosage is insufficient to produce substantial breast enlargement of the animals receiving the same.

8. The method of claim 1 wherein the duration of said temporary increase of the levels of said estradiol ester and said progesterone ester in the animals being treated does not exceed about 30 days.

9. The method of claim 1 wherein said meat-producing non-ruminant animals are pigs.

10. The method of claim 6 wherein said liquid vehicle is an oily carrier.

* * * * *